US006433021B1

(12) United States Patent
Frankish et al.

(10) Patent No.: US 6,433,021 B1
(45) Date of Patent: Aug. 13, 2002

(54) INDANE COMPOUNDS AND THEIR PHARMACEUTICAL USE

(75) Inventors: Neil Frankish; Helen Sheridan, both of Dublin; John Walsh, Ballingrube; Michael Jordan, Dublin, all of (IL)

(73) Assignee: Venantius Limited, Dublin (IL)

( * ) Notice: Subject to any disclaimer, the term of this patent is extended or adjusted under 35 U.S.C. 154(b) by 0 days.

(21) Appl. No.: 09/453,444

(22) Filed: Dec. 3, 1999

(30) Foreign Application Priority Data

Jun. 5, 1999 (IL) .................................................. 970422

(51) Int. Cl.[7] ...................... A61K 31/12; A61K 31/045; C07C 229/00; C07C 321/00; C07C 49/115
(52) U.S. Cl. ........................ 514/677; 514/681; 514/727; 514/728; 514/730; 514/732; 562/433; 562/427; 562/462; 562/466; 564/440; 564/443; 564/434; 568/327; 568/715
(58) Field of Search ................ 562/433, 427, 562/462, 466; 568/327, 715; 564/443, 440, 434; 514/677, 681, 727, 728, 730, 732

(56) References Cited

U.S. PATENT DOCUMENTS 2,837,571 A    6/1958   Conover

FOREIGN PATENT DOCUMENTS

| EP | 0183492 | 6/1986 |
| GB | 1380089 | 1/1975 |
| WO | WO92/21641 | 12/1992 |
| WO | WO97/20802 | 6/1997 |

OTHER PUBLICATIONS

Wachsen et al, "Acylgruppenwanderung, V Kinetische . . . ", Chem. Ber., vol. 108, pp. 683–692, 1975.
Dehmlow et al, "Über die Bildung von Indanonderivaten . . . ", Liebigs Ann. Chem., pp. 1617–1624, 1977.
Keller et al, "Ytterbium triflate catalyzed Michael additions of . . . ", Tetrahedron Lett., vol. 37 pp. 1879–1882, 1996.
Negishi et al, "Carbonylative cyclization via intramolecular trapping . . . ", J. Am. Chem. Soc., pp. 8018–8020, 1989.
Herman et al, "Polymergebundene Cinchonaalkaloide als . . . ", Helv. Chim. Acta, vol. 60, pp. 2208–2212, 1977.
Grigg et al, "Palladium catalyzed cascade carbonylation– . . . ", Tetrahedron Lett., vol. 35, pp. 7661–7664, 1994.
Muerling, "Isolation of the various setereoisomers of 2–benzoyl 2–methyl–1–ind . . . ", Chem. Scr., vol. 27, pp. 355–357, 1987.
Cragoe, Jr. et al, "Agents for the treatment of brain edema . . . ", J. Med. Chem., vol. 29, pp. 825–841, 1986.

*Primary Examiner*—Alan Siegel
(74) *Attorney, Agent, or Firm*—Jacobson Holman, PLLC

(57) ABSTRACT

Indane compounds of general formulae (1) to (4) and their pharmaceutical use, particularly to achieve mast cell stabilising activity and/or anti-inflammatory activity are described. In these formulae $R^1$ to $R^7$ may be selected from: H, halo, hydroxy, alkoxy, aryloxy, acetoxy, carboxy, cyclopentyl, alkyl carbonyl, hydro carbonyl, amino, amido, alkylamino, hydroxyamino, amine oxide groups, azo groups, cyano, hydrazino groups, hydrazide groups, hydrazone groups, indane, indene, imide groups, iminoether groups, ureyl groups, oxime, nitro, nitrate, nitrite, nitroso groups, nitirile, heterocyclic groups containing hetero atoms selected from one or more of N, O or S, aralkyl groups, aryl groups, mono and polybenzoid aryl groups, substituted aryl groups, thiol, thioureyl, phenylthiol groups, sulphonic acid groups, sulphoxide groups, sulphone groups, carboxylic acid groups of $C_1$ to $C_{10}$ which may be substituted or unsubstituted, alkyl, substituted alkyl groups, acyl groups, substituted acyl groups; where $R^1$ and $R^3$ may together represent a double bond and wherein in $(CH_2)_n$, n is 0 to 8.

5 Claims, No Drawings

INDANE COMPOUNDS AND THEIR PHARMACEUTICAL USE

The invention relates to indane compounds, process for their production, compositions containing them and their pharmacological use. More particularly, the invention relates to 2-[2-indenyl]indanones and 2-cyclopentenyl compounds as anti-inflammatory agents and mast cell stabilisation agents. According to the invention, there is provided a compound of any of the formulae 1–4.

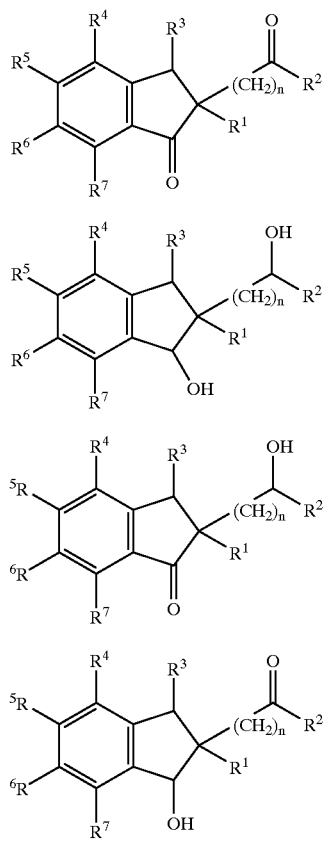

wherein $R^2$ to $R^7$ are selected from the group consisting of: hydrogen; hydroxy; cyclopentyl; alkyl carbonyl; hydro carbonyl; amino; amido; alkylamino; hydroxyamino; amine oxide groups; cyano; indane; indene; oxime; heterocyclic groups containing hetero atoms selected from one or more of N, 0 or S; aralkyl groups; aryl groups; mono and polybenzoid aryl groups; substituted aryl groups; thiol; thioureyl; phenylthiol groups; sulphonic acid groups; sulphoxide groups; sulphone groups; carboxylic acid groups of Cl to $C_{10}$ which may be substituted or unsubstituted; alkyl; substituted alkyl groups; acyl groups; and substituted acyl groups; where $R^1$ and $R^3$ may together represent a double bond and wherein in $(CH_2)_n$, n is 0 to 8.

Preferred because of solubility salt formation, pharmacological activity and/or ease of production are the following subsets.

In one embodiment of the invention the compound is of the formula 2 as defined in claim 1.

In a further embodiment of the invention the compound is of the formula 3 as defined in claim 1.

In a preferred embodiment of the invention $R^1$ to $R^7$ are selected from one or more of the same or different of:

hydroxy, alkyl of $C_1$ to $C_{10}$, aryl, substituted aryl, cyclopentyl, alkyl carbonyl, hydro carbonyl, amimo, amido, alkalamnino, hydroxyamino, amide oxide groups, cyano, indane, indene, oxime, sulphonic acid groups, sulphoxide groups, sulphone groups, or heterocyclic groups containing hetero atoms selected form one or more of N, O.

Preferably $R^4$ to $R^7$ are hydrogen.

In one preferred embodiment of the invention $R^1$ is cyclopentyl.

In this case preferably $R^1$ is cyclopenryenyl.

In one preferred aspect $R^1$ is indane.

In another preferred aspect $R^1$ is indene.

In one arrangement $R^2$ is acyl containing 1 to 10 carbon atoms.

Alternatively, $R^2$ is alkyl containing 1 to 10 carbon atoms, preferably, $C_1$ alkyl.

In another embodiment of the invention $R^2$ is substituted alkyl.

In a further embodiment of the invention $R^2$ is aryl having 4 to 8 carbon atoms, especially $C_1$ aryl.

The invention especially provides the following specific compounds:

1-phenyl-2-((2'-iidenyl)-indan-2-onyl)ethan-1-one (Compound I)

1-phenyl-2-((2'-iindenyl)-indan-2-ol)ethan-1-ol (Compound II)

1-phenyl-2-((2'-iidenyl)-indan-2-ol)ethan-1-one (Compound III)

1-phenyl-2-((2'-iidenyl)-indan-2-one)ethan-1-ol (Compound IV)

1-phenyl-2-((2'-cyclopent-1-enyl)indan-1-one)ethan-1-one (Compound V)

1-((2'-iindenyl)-indan-2-one)propan-2-one (Compound VI)

1-((2'-iindenyl)-indan-2-ol)propan-2-ol (Compound VII)

1-((2'-iindenyl)-indan-2-one)propan-2-ol (Compound VIII)

1-((2'-iindenyl)-indan-2-ol)propan-2-one (Compound IX)

The compounds may be used particularly to achieve mast cell stabilising and/or anti-inflammatory activity.

The invention also provides processes for preparing the compounds as defined in claims 33 to 42.

It will be appreciated that the compounds include pharmacologically acceptable salts, esters, amides, isomers and solvates thereof.

It will also be appreciated that if the compounds have one or more chiral centres they may exist as a pair of enantiomers or as a mixture of diastereomers. This may have an effect on pharmacological properties.

It will further be appreciated that for pharmaceutical purposes the active compounds may be formulated in any desired form using any suitable excipients and/or carriers. For example, particularly in the case for use to achieve anti-inflammatory activity the compound may be formulated in a pharmaceutical composition suitable for topical/transdermal application.

The invention will be more clearly understood from the following description thereof, given by way of example only.

DETAILED DESCRIPTION OF THE INVENTION

In the preparation of some of the compounds of the invention are described in detail below. Some of the starting materials used are described in our earlier applications PCT/IE96/00080, PCT/IE96/00081 and PCT/IE96/00082 the contents of which are incorporated herein for reference. Other compounds within the scope of the claims can be prepared by analogy.

EXAMPLE 1

Preparation of Compound I (Method A)

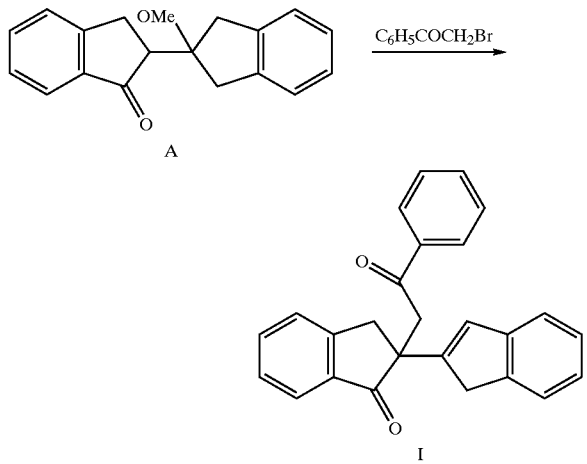

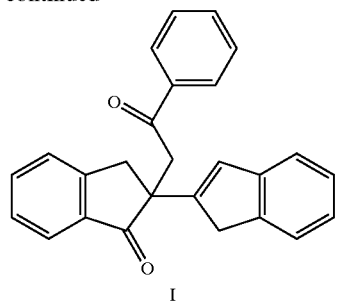

Compound A (1 g, 3.6 mmol) was dispersed in $^t$BuOH;Et$_2$O (1:9, 20 ml), and to this was added phenacyl bromide (3.58 g, 18 mmol). To this solution, which was stirred at room temperature, potassium tert butoxide (1 g) in $^t$BuOH:Et$_2$O (9:1 20 ml) was added dropwise. The crude reaction mixture was extracted into ethyl acetate. The product I was isolated by column chromatography eluting with petroleum ether:ethyl acetate (9:1) (0.98 g, 75%).

$^1$H nmr (δCDCl$_3$, 400 MHz) 3.35 (1H, d, J=22.5Hz,CH of CH$_2$), 3.54 (2H, t, J=14.5Hz, CH$_2$), 3.69 (1H,d, J=17.1 Hz, CH of CH$_2$), 3.99 (2H, q, J=18.7Hz, CH$_2$) 6.79 (1H,s,C=C H), 7.16–8.04 (13H,m, Ar—CH)

$^{13}$C nmr (CDCl$_3$, 75.47 MHz) 38.3, 39.7, 40.9 (3×CH$_2$), 53.1 (qC), 120.3, 123.1, 124.2, 124.3, 125.9, 126.0, 126.4, 127.2, 127.7, 127.8, 128.1, 128.3, 128.4, 133.0 (13×Ar—CH & 1×C=CH), 135.3, 136.1, 142.5, 143.8, 148.2, 152.0, (5×Ar—C & 1×C=CH), 196.7, (CH$_2$COC$_6$H$_5$), 204.8 (CO)

EXAMPLE 2

Preparation of Compound I (Method B)

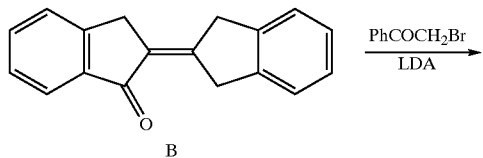

Compound B (100 mg, mmol) was dispersed in THF in a clean dry 3-necked flask under nitrogen, which was cooled to −78° C. To this was added LDA (2 equivalents). After stirring for 10 minutes at −78° C. phenacyl bromide (4 equivalents) was added and the solution was allowed to warm to room temperature and stirred for 3 hours. The product I was isolated by column chromatography eluting with petroleum ether: ethyl acetate (9:1) (0.38 mg, 17%)

$^1$H nmr (δCDCl$_3$ 400 MHz) 3.35 (1H,d, J=22.5Hz, CH of CH$_2$), 3.54 (2H, t, J=14.5Hz, CH$_2$), 3.69 (1H, d, J=17.1 Hz, CH of CH$_2$), 3.99 (2H,q, J=18.7Hz, CH$_2$), 6.79 (1H, s, C=C H), 7.16–8.04 (13H,m Ar—CH)

$^{13}$C nmr (CDCl$_3$, 75.47 MHz) 38.3, 39.7, 40.9 (3×CH$_2$), 53.1(qC), 120.3, 123.1, 124.2, 124.3, 125.9, 126.0, 126.4, 127.2, 127.7, 127.8, 128.1, 128.3, 128.4, 133.0 (13×Ar—CH & 1×C=CH), 135.3, 136.1, 142.5, 143.8, 148.2, 152.0 (5×Ar—C & 1×C=CH), 196.7 (CH$_2$COC$_6$H$_5$), 204.8 (CO)

EXAMPLE 3

Preparation of Compound II

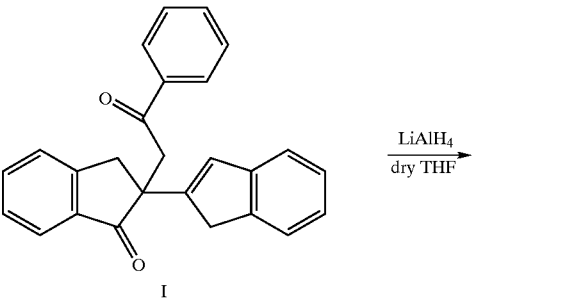

Compound I (300 mg, 0.8 mmol) was dissolved in clean dry THF (10 ml) and to this was added lithium aluminium hydride (300 mg. 8 mmol). The crude product was extracted into ethyl acetate. The product II was obtained as a mixture of diastereomers by column chromatography eluting with petroleum ether:ethyl acetate (9:2) (0.175 g, 58%)

Low resolution mass Spectrum
$C_{26}H_{24}O_2$, require $M^+368$, Found $M^+368$ $^1H$ nmr ($\delta CDCl_3$, 400 MHz) 1.97 (1H, bs, CHOHCH$_2$), 2.09 (1H, bs, CHOH), 2.13–2.36 (2H, m, CH$_2$), 3.12 (1H, d, J=22.6Hz, CH of CH$_2$), 3.46–3.52 (2H, m, (CH$_2$), 3.55 (1H, d, J=23.2Hz, CH of CH$_2$), 4.77 (1H, m, CHOHCH$_2$), 4.96 (1H, s, CHOH), 6.79 (1H, s, C=CH), 7.15–7.41 (13H, m, Ar—CH).

$^{13}C$ nmr (CDCl$_3$, 75.47 MHz) 40.5, 40.7, 46.7 (3×CH$_2$), 55.4 (qC), 76.6, 83.4 (2×CHOH), 120.5, 123.5, 124.2, 124.3, 124.8, 125.5, 125.5, 125.8, 125.8, 126.3, 126.8, 127.5, 128.4, 128.5, 130.4, (13×Ar—CH & 1×C=CH), 141.5, 143.0, 143.1, 144.1, 145.4, 150.2, (5×Ar—C & 1×C=CH)

EXAMPLE 4

Preparation of Compounds III and IV

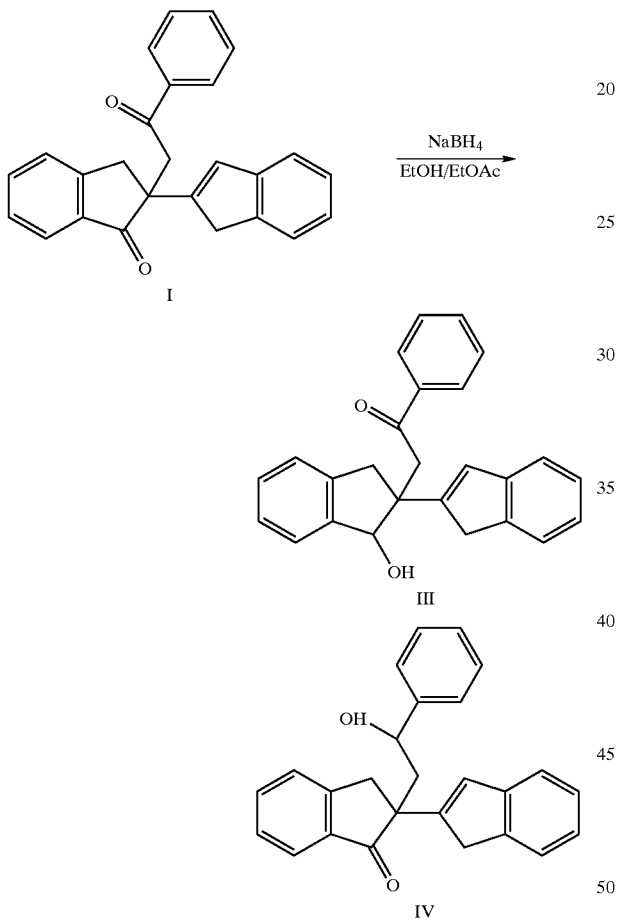

Compound I (300 mg, 0.8 mmol) was dispersed in ethanol ethyl acetate (9:1, 20 ml) and to this was added sodium borohydride (16 mg, 0.42 mmol). The crude product was extracted into ethyl acetate. Three products were observed by TLC (II, III and IV). The product was isolated by column chromatography eluting with petroleum ether: ethyl acetate (9:1), (Compound III trace amount), (Compound IV, 0.027 g, 9%).

Compound III

Low resolution mass Spectrum $C_{26}H_{24}O_2$ requires $M^+366$, Found $M^+366$.

$^1H$ nmr ($\delta CDCl_3$, 400 MHz) 3.31–3.95 (6H, m, 3×CH$_2$), 4.17 (1H, s, CHOH), 6.75 (1H, s, C=CH), 7.17–8.05 (13H, m, Ar—CH)

Compound IV

Low resolution mass spectrum $C_{26}H_{24}O_2$ requires $M^+366$, Found $M^+366$ $^1H$ nmr ($\delta CDCl_3$, 400 MHz) 3.21 (2H, s, CH$_2$), 3.56 (2H, d, J=5.8 Hz, CH$_2$), 3.83 (2H, q, J=17.9 Hz, CH$_2$), 5.31 (1H, s, CHOH), 6.49 (1H, s, C=CH), 6.88–8.07 (13H, m, AR-CH)

$^{13}C$ nmr (CDCl$_3$, 75.47 MHz) 40.2, 43.6, 47.3 (3×CH$_2$), 53.5 (qC), 82.3 (2×CHOH), 120.3, 123.3, 124.1, 124.2, 124.3, 126.0, 126.3, 127.1, 128.1, 128.3, 128.9, 133.5 (13× Ar—CH & 1×C=CH), 136.7,139.7,142.7, 143.4, 143.7, 150.3 (5×Ar—C & 1×C=CH), 202.3 (CO)

EXAMPLE 5

Preparation of Compound V

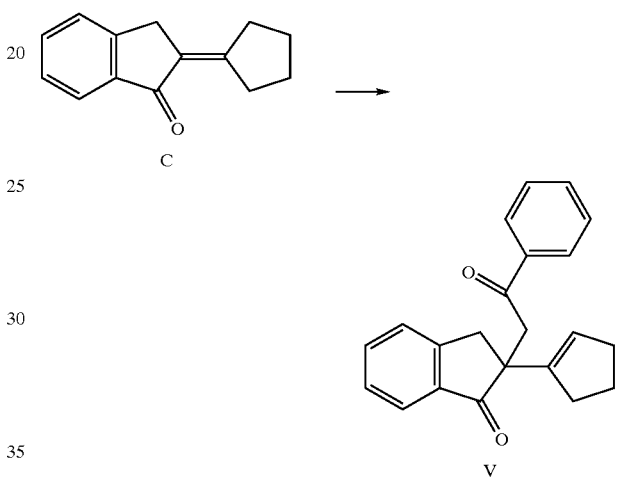

Compound C (400 mg) was dissolved in clean dry THF (20 ml) at −78° C. to this was added LDA (0.8 ml) and the mixture was stirred at −78° C. for 10 minutes. Phenacyl bromide (1.43 ml. 10 equivs) was added and the solution was allowed to warm to room temperature and stirred for 3 hours under nitrogen.

The crude product was extracted into ethyl acetate. The product V was obtained by column chromatography eluting with petroleum ether: ethyl acetate (9:2) (0.12 mg, 7%).

Compound V

Low resolution mass Spectrum $C_{22}H_{20}O_2$ requires $M^+316$, Found M+316

$^1H$ nmr ($\delta CDCl_3$, 400 MHz) 1.18–1.84 (6H, m, 3×CH$_2$), 3.86–4.26 (4H m, x CH$_2$), 7.09–7.94 (10H, m, 1×C=CH, Ar—CH)

EXAMPLE 6

Compound VI

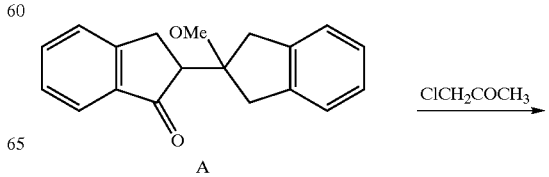

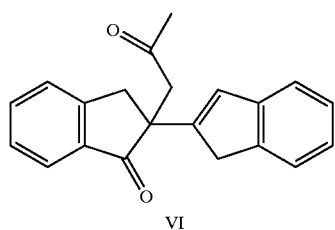

VI

Compound A (1 g, 3.6 mmol) was dispersed in $^tBuOH:Et_2O$ (1:9, 20 ml), and to this was added chloropropanone (8 ml). To this solution, which was stirred at room temperature, potassium tert butoxide (1 g) in $^tBuOH:Et_2O$ (9:1, 20 ml) was added dropwise. The crude reaction mixture was extracted into ethyl acetate. The product VI was isolated by column chromatography eluting with petroleum ether: ethyl acetate (9:1) (0.98 g, 75%).

Low resolution mass Spectrum

Requires $C_{21}H_{18}O_2$ $M^+302$ Found $M^+302$ $^1$H nmr ($\delta CDCl_3$, 400 MHz) 2.41 (3H, s, $COCH_3$), 3.21–3.40 (4H, m, 2×$CH_2$), 3.45 (1H, d, J=17.1 Hz, $CH$ of $CH_2$), 3.84 (1H, d, J=17.1 Hz, $CH$ of $CH_2$), 7.15–7.72 (9H, m, 8×Ar—$CH$ and C=$CH$)

Example 7

Compounds VII, VIII and IX

Compound VI (300 mg, 0.8 mmol) was dispersed in ethanol/ethyl acetate (9:1, 20 ml) and to this was added sodium borohydride (16 mg, 0.42 mmol). The crude product was extracted into ethyl acetate. Three products were observed by TLC (VII, VIII and IX). The products were isolated by column chromatography eluting with petroleum ether: ethyl acetate (9:1), (Compound VII, 73 mg), (Compound VIII, 27 mg), (Compound IX, 43 mg).

Compound VII $^1$H nmr ($\delta CDCl_3$, 400 MHz) 2.43 (3H, d, J=8 Hz, CHOHC$H_3$), 3.25–3.41 (4H, m, 2×$CH_2$), 3.47 (1H, m $CH$ of $CH_2$), 3.80 (1H, m, $CH$ of $CH_2$), 4.82 (1H, dq, $CH$OH), 5.01 (1H, s, $CH$OH), 7.111–7.69 (9H, m, 8×AR-$CH$ and C=$CH$)

Low resolution mass Spectrum

Requires $C_{21}H_{22}O_2$ $M^+306$ Found $M^+306$

Compound VIII $^1$H nmr ($\delta CDCl_3$, 400 MHz) 2.40 (3H, d, J=8Hz, CHOHC$H_3$), 3.25–3.41 (4H, m, 2×$CH_2$), 3.45 (1H, m $CH$ of $C_2$), 3.77 (1H, m, $CH$ of $CH_2$), 4.85 (1H, dq, $CH$OH), 7.10–7.65 (9H, m, 8×Ar—$CH$ and C=$CH$)

Low resolution mass Spectrum

Requires $C_{21}H_{20}O_2$ $M^+304$ Found $M^+304$

Compound IX $^1$H nmr ($\delta CDCl_3$, 400 MHz) 2.40 (3H, s, $COCH_3$), 3.23–3.40 (4H, m, 2×$CH_2$), 3.45 (1H, m, $CH$ of $CH_2$), 3.77 (1H, m , $CH$ of $CH_2$), 5.03 (1H,s, $CH$OH), 7.12–7.68 (9H, m, 8×Ar—$CH$ and C=$CH$)

Low resolution mass Spectrum Requires $C_{21}H_{20}O_2$ $M^+304$ Found $M^+304$

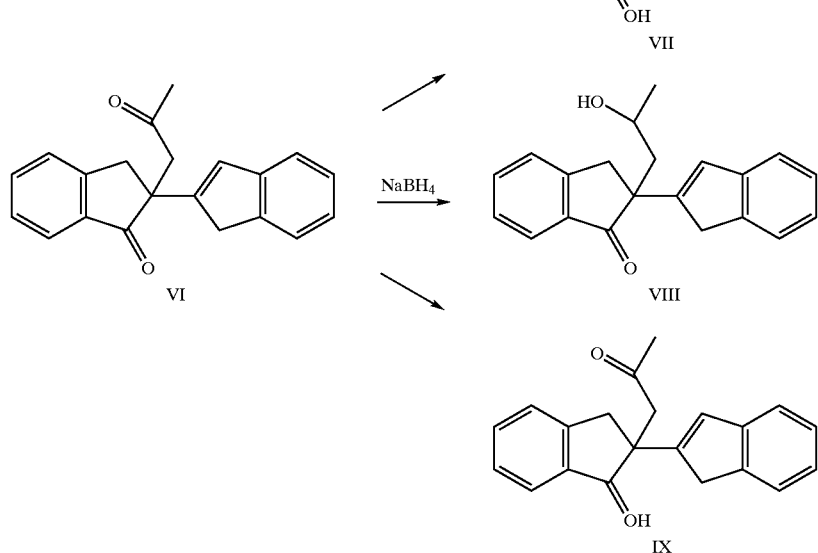

EXAMPLE 10

Compounds X, XI, XII

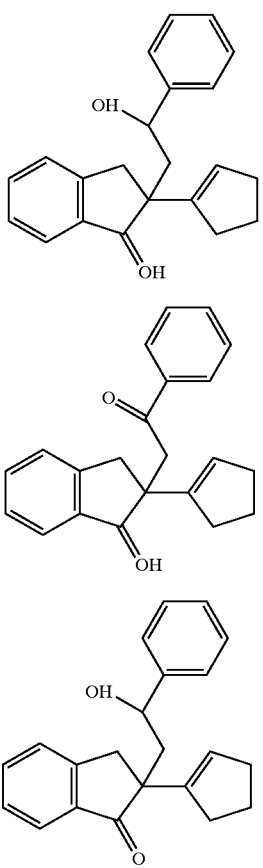

These compounds are similar to compound V. By virtue of the same chemistry used in the synthesis of compounds II, III and IV the compounds X, XI and XII would be expected. These compounds would be synthesised to a greater yield by a more efficient coupling stage in the formulation of the starting material.

PHARMACOLOGY

Introduction

The indane compounds according to the invention have mast cell stabilising activity and anti-inflammatory activity. The compounds are, therefore, potential anti-asthmatic agents with bronchodilator activity. The mast cell stabilising activity of the compounds suggest their potential use in the treatment of allergic rhinitis, allergic conjunctivitis and other anaphylactic or allergic conditions. The anti-inflammatory activity may have applications in gout, rheumatic diseases, ankylosing spondylistis, polymyalgia rheumatica, temporal arteritis, polyarteritis nodosa, polymyositis and systemic lupus arteriosis and other inflammatory conditions. Topical applications may include: atopic excema, weeping excemas, psoriasis, chronic discoid lupus erythematosus, lichen simplex chronicus, hypertrophic lichen planus, palmar plantar pustulosis. They may also have potential in the treatment of some malignant diseases and as immunosuppressants.

The compounds may also have smooth muscle relaxing activity which may have potential in the treatment of hypertension and peripheral vascular disease, such as intermittent claudication and Reynaud's syndrome, as well as other cardiovascular disorders, such as congestive heart failure, angina pectoris, cerebral vascular disease and pulmonary hypertension. Such compounds are also indicated for potential use in the treatment of certain disorders of the gastrointestinal tract, such as diverticular disease and irritable bowel syndrome. Similarly, these compounds may have potential as agents for the treatment of disorders of the genito-urinary tract, such as premature labour, incontinence, renal colic and disorders associated with the passage of kidney stones. Member of this group of compounds may also have potential as diuretics analgesics, antipyretics, local anaesthetics, central nervous system depressants and hypoglycaemic agents.

The compounds were assessed for their ability to stabilise mast cell membranes in vitro. Mast cells treated with the compounds and untreated mast cells were stimulated to release histamine. A reduction in histamine release by the treated cells compared to the untreated cells indicates stabilisation of the membranes.

There follows protocols of each of these assays and a summary of the results.

| ABBREVIATIONS | |
|---|---|
| BSS | buffered salt solution |
| $CaCl_2$ | calcium chloride |
| $CO_2$ | carbon dioxide |
| DMSO | dimethyl sulphoxide |
| DSCG | disodium cromoglycate |
| $dH_2O$ | distilled water |
| HCl | hydrochloric acid |
| HEPES | N-2-hydroxyethylpiperazine-N-2-ethanesulphonic acid |
| KCl | potassium chloride |
| λem | emission wavelength |
| λex | excitation wavelength |
| M | Molar |
| $MgCl_2$ | magnesium chloride |
| min | minutes |
| ml | microliters |
| mM | milli-molar |
| NaCl | sodium chloride |
| $NaHCO_3$ | sodium hydrogen carbonate |
| $NaH_2Po$ | sodium hydrogen phosphate |
| NaOH | sodium hydroxide |
| $O_2$ | oxygen |
| oPT | o-phthaldialdehyde |
| S.E.M | standard error of mean |
| w/v | weight per volume |
| v/v | volume per volume |

METHODS

Histamine Release Assay

The buffered salt solution (BSS) was prepared in advance (NaCl 137 mM; KCl 2.7 mM; $MgCl_2$ 1.0 mM; $CaCl_2$ 0.5 mM; $NaH_2PO_4$ 0.4 mM; Glucose 5.6 mM; HEPES 10 mM). This was dispensed into test tubes and heated to 37° C. each test tube contained 4.5 ml BSS. The solvent blank was supplemented with 0.5% (v/v) dimethyl sulphoxide (DMSO) or 0.5% (v/v) distilled water ($dH_2O$). The two positive controls were supplemented with 0.5% (v/v) DMSO/$2\times10^{-5}$ M disodium cromoglycate (DSCG) and 0.5% (v/v) DMSO/$2\times10^{-5}$ M test compound/0.5% (v/v) DMSO. The basal release, maximum release and total histamine content incubation tubes contained no additions.

Female Wistar rats (200–300 g) were killed in an atmosphere of saturated $CO_2$. Pre-warmed BSS (10 ml) was injected i.p. and the abdomen was massaged for 3 min. The BSS, with suspended mast cells and other cells, was aspirated following a mid-line incision. The aspirate was centrifuged for 5 min at 400 g and the supernatent removed. The cells were re-suspended in BSS, at 4° C., and centrifuged as before. The cells were washed in this manner a total of three times. Following the final wash, the pelleted cells were stored at 4° C., for use as soon as possible.

The cells were re-suspended in 7 ml BSS. From this, 0.5 ml aliquots were transferred to each of the incubation tubes. After 10 min at 37° C., with gentle agitation, Compound 48/80 was added to a final concentration of 2 mg/ml, in order to stimulate histamine release. The cell stimulation was stopped after 2 min by the addition of 0.5 ml ice cold BSS, the incubation tubes were transferred to an ice bath. The cell suspensions were centrifuged for 5 min at 400 g. The "total histamine content" rube was placed at 100° C. for 2 min prior to centrifugation. The supernatants were retained for histamine assay.

To 2 ml of supernatent from each tube was added 0.4 ml of 1 M NaOH and 0.1 ml oPT (1% (w/v) in methanol). This was incubated at room temperature for 4 min. The reaction was stopped by the addition of 0.2 ml of 3 M HCl. The supernatant from each incubation tube was assayed in duplicate and run simultaneously with a standard curve in the range 0–1000 mg/ml. The presence of the fluorescent product of the reaction was measured using a Shimadzu RF-1501 spectrofluorophotometer set at $\lambda ex=360$ nm, $\lambda em=450$ nm.

Each drug was tested on at least five animals (n=5). The results were expressed as a percentage of maximum inhibition of compound 48/80 induced-histamine release in the solvent blank sample. Each drug was compared to DSCG on the same tissues. The basal histamine release in untreated cells was noted, expressed as a percentage of the total histamine content of the cells in suspension.

| | Mast Cell | |
|---|---|---|
| Compound | % inhibition of histamine Release (±S.E.M.) | n (number) |
| II | 53.49 ± 2.53 | 5 |

Mouse Ear Oedema Model

The mouse ear oedema model was performed using Laca mice (25–35 g), of either sex. The animals were sedated with fentanyl/fluanisone (Hypnorn, Janssen). One ear was treated by the topical application of one of a range of test compounds or dexamethasone (all at 300 µg per ear in acetone). After 30 minutes, oedema was induced by the topical application of arachidonic acid (10 µl at 0.4 g/ml in acetone). The width of each ear was measured, both before and 60 minutes after the induction of oedema, using a micrometer screw gauge. Ear oedema was calculated by comparing the ear width before and after induction of oedema and expressed as percentage normal.

Values are expressed as the percentage increase in ear thickness 1 hour after administration of archidonic acid and solvent controls (n=6 except Compound IV, n=4).

Acute Inflammation—Mouse Ear

| Compound | Mean % | SEM | n (number) |
|---|---|---|---|
| Dexamethasone | 41.6 | 5.6 | 6 |
| I | 49.3 | 6.7 | 6 |
| Solvent Control | 69.0 | 5.8 | 6 |
| Dexamethasone | 54.0 | 6.2 | 6 |
| II | 17.7 | 5.6 | 6 |

-continued

| Compound | Mean % | SEM | n (number) |
|---|---|---|---|
| III | 37.3 | 6.0 | 6 |
| IV | 13.1 | 7.4 | 4 |
| Solvent Control | 79.6 | 12.8 | 4 |

The invention is not limited to the embodiments hereinbefore described which may be varied in detail.

What is claimed is:

1. A compound of any of the formulae 1 to 4

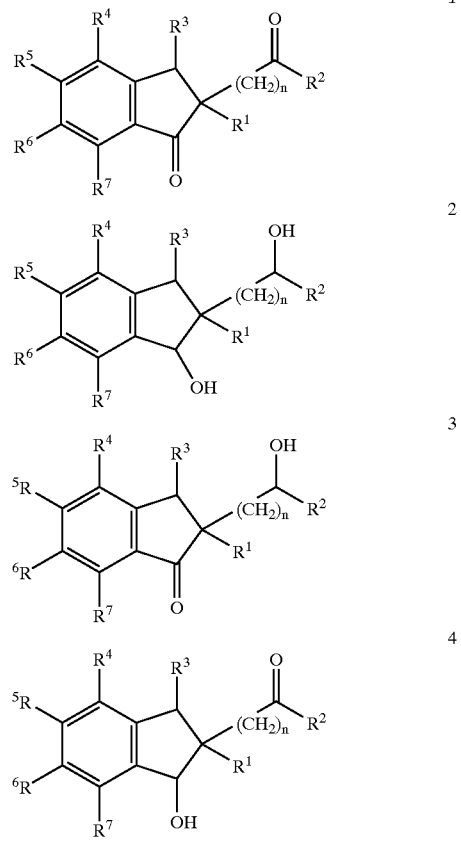

wherein $R^2$ to $R^7$ are each independently selected from the group consisting of:

hydrogen; hydroxy; cyclopentyl; alkyl carbonyl; hydro carbonyl; amino; amido; alkylamino; hydroxyamino; amine oxide groups; cyano, indane; indene; oxime; heterocyclic groups containing hetero atoms selected from one or more of N or O; aryl groups; mono and polybenzoid aryl groups; substituted aryl groups; sulphonic acid groups; sulphoxide groups; sulphone groups; alkyl; substituted alkyl groups; acyl groups; and substituted acyl groups;

wherein in $(CH_2)_n$, n is 0 to 8; and $R^1$ is selected from the group consisting of cyclopentyl, cyclopentenyl, indane, indene, and substituted derivatives thereof.

2. The compound of claim 1, wherein $R^4$ to $R^7$ are hydrogen.

3. A compound as claimed in claim 1, wherein $R^2$ is acyl or alkyl containing 1 to 10 carbon atoms, $C_1$ alkyl, substituted alkyl or $C_6$ aryl.

4. The compound of claim 1 selected from the group consisting of:

1-phenyl-2-((2'-iidenyl)-indan-2-onyl)ethan-1-one;
1-phenyl-2-((2'-iidenyl)-indan-2-ol)ethan-1-ol;
1-phenyl-2-((2'-iidenyl)-indan-2-ol)ethan-1-one;
1-phenyl-2-((2'-iidenyl)-indan-2-one)ethan-1-ol;
1-phenyl-2-((2'-cyclopent-1-enyl)indan-1-one)ethan-1-one;
1-((2'-iindenyl)-indan-2-one)propan-2-one;
1-((2'-iindenyl)-indan-2-ol)propan-2-ol;
1-((2'-iindenyl)-indan-2-one)propan-2-ol; and
1-((2'-iindenyl)-indan-2-ol)propan-2-one.

5. A pharmaceutical composition comprising the compound of claim 1 and a pharmaceutically acceptable carrier.

* * * * *